United States Patent [19]
Loewy et al.

[11] Patent Number: 6,004,752
[45] Date of Patent: Dec. 21, 1999

[54] SOLID SUPPORT WITH ATTACHED MOLECULES

[75] Inventors: Zvi Gerald Loewy, Fair Lawn; Bawa Singh, Vorhees, both of N.J.

[73] Assignee: Sarnoff Corporation, Princeton, N.J.

[21] Appl. No.: 08/956,348

[22] Filed: Oct. 23, 1997

Related U.S. Application Data

[60] Provisional application No. 60/054,071, Jul. 29, 1997.

[51] Int. Cl.[6] ........................................................ C12Q 1/68
[52] U.S. Cl. .............................. 435/6; 435/91.2; 536/24.3
[58] Field of Search ....................... 435/6, 91.2; 536/24.3

[56] References Cited

U.S. PATENT DOCUMENTS

| | | |
|---|---|---|
| 4,072,129 | 2/1978 | Bright et al. . |
| 4,088,093 | 5/1978 | Pan . |
| 4,160,257 | 7/1979 | Carrish . |
| 4,197,289 | 4/1980 | Sturzenegger et al. . |
| 4,332,789 | 6/1982 | Mlodozeniec . |
| 4,342,566 | 8/1982 | Theofilopoulos et al. . |
| 4,349,531 | 9/1982 | Mlodozeniec et al. . |
| 4,538,163 | 8/1985 | Sherldon . |
| 4,685,620 | 8/1987 | Law et al. . |
| 4,779,564 | 10/1988 | Kiefer et al. . |
| 4,889,816 | 12/1989 | Davis et al. . |
| 4,917,978 | 4/1990 | Ritt et al. . |
| 4,918,468 | 4/1990 | Miekka et al. . |
| 4,921,727 | 5/1990 | Datta et al. . |
| 4,921,767 | 5/1990 | Datta et al. . |
| 4,956,150 | 9/1990 | Henry . |
| 4,971,257 | 11/1990 | Birge . |
| 4,992,807 | 2/1991 | Thomson . |
| 5,014,076 | 5/1991 | Caley, Jr. et al. . |
| 5,027,136 | 6/1991 | Fotland . |
| 5,028,501 | 7/1991 | Ritt et al. . |
| 5,278,588 | 1/1994 | Kubelik . |
| 5,364,593 | 11/1994 | Mihaylov et al. . |
| 5,434,049 | 7/1995 | Okano et al. ................................ 435/6 |
| 5,464,588 | 11/1995 | Bäther et al. . |
| 5,501,841 | 3/1996 | Lee et al. . |
| 5,554,517 | 9/1996 | Davey et al. ......................... 435/91.21 |
| 5,863,502 | 1/1999 | Southgate .................................. 422/58 |

FOREIGN PATENT DOCUMENTS

| | | |
|---|---|---|
| 59-150760 | 8/1984 | Japan . |
| 2 253 164 | 9/1992 | United Kingdom . |

OTHER PUBLICATIONS

Bate et al., *The Science of Powder Coatings,* vol. 2, pp. 69–71, (1994).

*Primary Examiner*—Scott W. Houtteman
*Attorney, Agent, or Firm*—William J. Burke

[57] ABSTRACT

Provided is a solid support having a composition of at least one compound deposited thereon by electrostatic or controlled field deposition, wherein the compound is attached to the support. Also provided is a method of preparing the solid support by creating an electromagnetic force for attracting particles having a first charge to a surface of the solid support and contacting the surface with the charged particles, which comprise the composition, and thereby coating the surface with the composition. Further provided is a probe array comprising spatially resolved probes deposited and attached on a solid support by electrostatic or controlled field deposition. These methods, supports and arrays provide the building blocks for methods of nucleic acid amplification and for constructing apparatuses for conducting chemical processes.

19 Claims, 3 Drawing Sheets

SOLID SUPPORT WITH ATTACHED MOLECULES

This application claims the benefit under 35 U.S.C. § 119(e)(1) of provisional patent application Ser. No. 60/054,071, filed Jul., 29, 1997.

The present invention relates to improved methods of attaching reagents to solid supports and assays conducted with reagents that are attached to solid supports.

In the field of assays, for example diagnostic assays, and other chemical processes it is frequently necessary to attach molecules, particularly but not exclusively macromolecules, to a solid support. The attached molecules often serve as capture conduits for a desired target. For example, in immunodiagnostics, proteins, protein derivatives or protein analogs are commonly attached to solid matrices. In another example, nucleic acids, nucleic acid derivatives or nucleic acid analogs are often attached to solid matrices to support a nucleic acid-based assay. These solid matrices include membranes, microwell plates, and particles such as microparticles.

Techniques for forming the attachments are well developed. For example molecules are attached by passive adsorption or through covalent linkages. In some cases a first chemical is attached to a solid support, and this first chemical is used to then bind a second compound, which is thereby attached to the support via the intermediary first compound. The avidin (or streptavidin)-biotin binding system has been used extensively to provide this kind of mediated binding to a solid support. For example, avidin-biotin systems can use biotin that is covalently linked to the second compound and avidin attached to the solid support, such that the second compound becomes attached via the strong binding of biotin to avidin.

What is needed in the art, however, are methods to enhance the amount of material that attaches to a solid support and to increase the reliability and reproducibility with which materials are applied to a solid support.

SUMMARY OF THE INVENTION

In one embodiment, the invention provides a solid support having a composition of at least one compound deposited thereon by electrostatic or controlled field deposition, wherein the compound is attached to the support. In another embodiment, the invention provides a method of preparing the solid support by creating an electromagnetic force for attracting particles having a first charge to a surface of the solid support and contacting the surface with the charged particles, which comprise the composition, and thereby coating the surface with the composition.

In a third embodiment, the invention provides a probe array comprising spatially resolved probes deposited and attached on a solid support by electrostatic or controlled field deposition.

In another embodiment, the invention provides a solid support for nucleic acid amplification on which are deposited at one or more locations either one or both of: one or more reagents, which can include primers, that support a nucleic acid amplification reaction; or at least one primer, wherein the deposited primer(s) are attached to the solid support.

The invention further provides a method of nucleic acid amplification comprising: providing one or more primers for the amplification wherein at least one primer is attached to a solid support, contacting with the solid support a sample material that prospectively contains a target nucleic acid from which a amplicon nucleic acid can be amplified as specified or directed by the primers, and amplifying the amplicon nucleic acid sequence if the sample contains the target nucleic acid.

In a further embodiment, the invention provides an apparatus and associated methods for conducting a chemical processes.

DEFINITIONS

Figure 1:
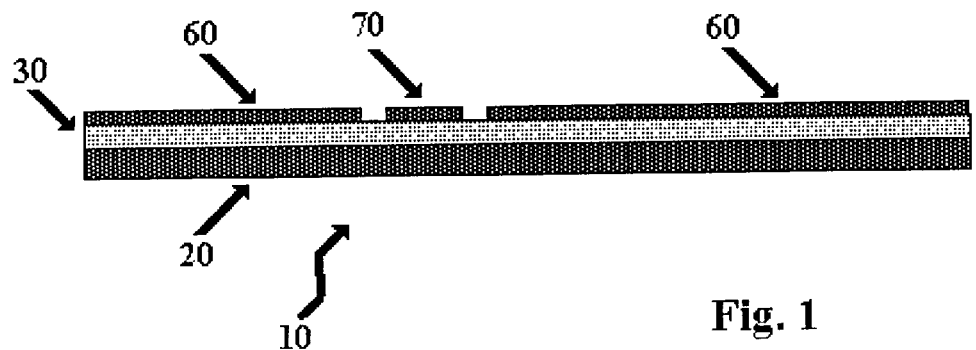
FIG. 1 displays a floating electrode apparatus.

The following terms shall have, for the purposes of this application, the meaning set forth below. In particular, for the purpose of interpreting the claims, the term definitions shall control over any assertion of a contrary meaning based on other text found herein:

Attached

By "attached," "attachment," "attaching" and related words, the Applicants refer to bonding or adsorption of a compound to a surface of a solid support of sufficient strength so that a liquid-solid phase chemical process can be conducted at the surface with the premise that compound will remain bonded to the solid support, or at least that sufficient amounts of the compound will remain bonded so as not to undermine the intent of the process. For example, a chemical process may be premised on the surface-bonded compound not being extracted into a contacting liquid, since for example the surface-bonded compound would not be favorably present during later liquid-phase steps of the process; however, the degree to which extraction into the contacting liquid is detrimental will depend on the particular process. Similarly, a chemical process may be premised on having sufficient amounts of the surface-bonded compound remaining available to play a role in generating a surface-associated detection signal. In a preferred embodiment, at least about 10% of the of the compound remains bonded to the surface after the chemical process, more preferably at least about 20% remains bonded, still more preferably at least about 50% remains bonded, yet still more preferably at least about 80% remains bonded, and still yet more preferably at least about 95% remains bonded. In a particularly preferred embodiment, in excess of about 99% of the surface-bonded compound remains bonded after the chemical process.

Dry deposited

A material is "dry deposited" if deposited without applying the material in a liquid vehicle.

Nomenclature for covalently attached compounds

Where a compound is to be attached to a solid support by a covalent bond, this bond necessarily implies that the compound which is initially deposited and that which is eventually attached to the support are not, in a strict chemical sense, the same. However, for the purposes of this application the deposited compound and the derivative formed in covalently attaching to the solid support are sufficiently the same, particularly where the property of the compound of interest is maintained in the support-attached form.

Nucleic Acid

The nucleic acid sequences used in the invention are preferably deoxyribonucleic acid sequences. However, they can also be ribonucleic acid sequences, or nucleic acid analogs, meaning compounds designed to preserve the hydrogen bonding and base-pairing properties of nucleic acid, but which differ from natural nucleic acid in, for example, susceptibility to nucleases.

Primer

A relatively short single-stranded nucleic acid that serves as a sequence-specific probe in a nucleic acid amplification reaction. The "primer" may be a nucleic acid polymerase primer in the strictest sense, in that it anneals to a strand of target nucleic acid and serves as a starting primer polymer that is extended by the activity of the polymerase, or it can serve as the probe in some other fashion, such as being subject to a ligase catalyzed ligation when it anneals to an appropriate nucleic acid.

Probe

A probe is any compound attached to a solid support that is used to mediate at least a portion of a chemical process.

Substantially delayed

"Substantially delayed" from dissolving in the second liquid means delayed sufficiently so that, so long as the sample is added to a given well or other reaction vessel prior to a designated time period, a time-sensitive the assay can be conducted based on the time that the first liquid was added to the well rather than the time at which the sample was added.

DETAILED DESCRIPTION OF THE INVENTION

The advantages of the invention are achieved by initially depositing the compounds to be attached to the support by electrostatic or "controlled field" deposition. These techniques allow for reproducible and controlled depositions of materials, and facilitate the processes by which the deposition matures to create attached molecules.

Electrostatic and controlled field deposition techniques have been used to deposit medicaments onto substrates. In making dry powder inhalers for medicaments, it is desirable to have the post-deposition material relatively loosely bonded to the substrate. However, unless certain precautions are undertaken, compounds that are deposited by electrostatic and controlled field deposition tend to become with time more and more tightly bonded to the substrate. U.S. application Ser. No. 08/661,213, filed Jun. 10, 1996 addresses this issue, which is a potential problem with respect in inhalers (this application is incorporated herein by reference in its entirety). However, for the present purposes this bonding effect is positive since the tight association observed facilitates the formation of attachments of a compound to a solid support.

The discussion below describes depositions made for the purpose (a) of attaching one or more chemicals to a solid support or (b) depositing a layer of releasable reagents, such as can support a chemical process. While a primary focus of the present disclosure is on solid supports with attached compounds, such solid supports can be used in assays or other chemical processes where it is convenient to have further deposited on the solid support metered amounts of process supportive reagents which are ready for use by, for example, merely adding the appropriate liquid. Concurrently filed herewith is a copending patent application Docket No. SAR 12522, entitled "Deposited Reagents for Chemical Processes", Loewy et al., which describes methods for depositing metered amounts of reagents as a set-up pool of reagents to support a chemical process. This concurrently filed application is incorporated herein by reference in its entirety.

A. Manufacturing Solid Supports with Attached Compounds

1. Electrostatic and Controlled Field Deposition

In electrostatic deposition methods a substrate is sufficiently electrically isolated so that an electrostatic charge can be accumulated on the substrate. One means of accumulating the charge is by taking advantage of the photoelectric effect. In this method the substrate is exposed to electromagnetic radiation effective to strip charges, typically electrons, from the surface of the substrate. Other methods include tribocharging and plasma treatment. In a more preferred method, an ion emitter is oriented towards the surface on which one intends to create a charge and operated. Such methods of ion printing to controllably electrostatically deposit charged materials such as powders are described in detail in U.S. application Ser. Nos. 08/471,889 (filed Jun. 6, 1995), 08/659,501 (filed Jun. 6, 1996) and 08/733,525 (filed Oct. 18, 1996), which documents are incorporated by reference herein in their entirety.

It should be noted that where the average charge-to-mass ratio of the charged particles of the deposition material is known, the mass of particles that will effectively deposit can be relatively accurately predicted from the amount of charge previously accumulated on the substrate. In particular, for a given type of substrate a calibration database can be compiled. For a given average charge-to-mass ratio of the applied particles, the relationship of accumulated charge to deposited mass is typically linear. In a production protocol, the average charge-to-mass ratio of the particles can be monitored, for instance using the velocimeter and a modified quartz crystal monitor described in U.S. application Ser. Nos. 08/661,211 and 08/661,210, both filed Jun. 10, 1996, which documents are incorporated herein by reference in their entirety. The illustrative charge-to-mass monitor functions by applying a voltage to a crystal such as a quartz crystal to establish a vibratory frequency, monitoring changes in the vibratory frequency when exposed to the charged particles, and correlating these changes to the mass of the particles that impact the monitor. Another charge-to-mass monitor uses the cage blowoff method of C. B. Schein and J. Cranch, *J. Applied Phys.* 46: 5140, 1975. With the use of one or more charge-to-mass monitors, feedback loops can be incorporated into the electrical controls of a deposition apparatus. In one preferred embodiment, a charge-to-mass monitor is positioned so as to sample the charge-to-mass of particles at their source (examples for source devices described below) and a charge monitor (for example a device for measuring currents created by the deposition of charged particles) is positioned adjacent to the site of deposition. The sampling values produced at these two sites provide diagnostic data on the operation of the deposition apparatus.

A number of additional methods can be used to monitor the amount of material that is deposited on a solid support. For example, optical methods can include measuring reflectance, transmission, or fluorescence using laser or non-collimated light of broad or narrow band width. Other sources of directed electromagnetic energy can be used, for instance X-ray absorption or fluorescence or microwave absorption can be used. A tuned circuit can be used to monitor an endpoint at which deposited material creates a resonance with an energy source such as a microwave energy source. Acoustic absorption can also be used, where preferably the sound source is an ultrasound source. Another exemplary measuring method can use a profilameter, which is a laser device that measures the amount the a beam of light is deflected by a surface with deposited material to measure the depth of the deposited material. Further electrical methods can include measuring a capacitance between a conductive material associated with the solid support (for example a conductive material incorporated into the solid support or a conductive material that has the solid support positioned adjacent to it) and another conductor, where the deposited material is located between the two conductors.

A variety of additional factors can be monitored or controlled to increase the reproducibility of the charge-to-mass ratios generated by the charged deposition material source. For example, the humidity of the local environment and the bound solvent content of the materials sought to be deposited, and the rubbing velocity effected in the tribocharging process can be important.

Another method of attracting charged deposition materials to a surface has been termed "controlled field deposition," and typically involves applying a potential to an electrode which directly or indirectly results in the formation of an attractive electrical field at the surface upon which charged material will be deposited. For example, a substrate can have electrical conductors positioned below the deposition surfaces, and a potential applied to the conductors results in the formation of an attractive field at the surface. Where the separation between the substrate's surface and the conductors is sufficiently small, once an external potential is no longer applied to the conductors the charge of the deposition material results in a charge redistribution in the conductors such that an electrostatic "image" force is formed between the deposition material and the conductors, thereby helping to stabilize the deposition material's adherence to the surface.

Further examples of field-generating means include the use of "floating electrodes." A floating electrode is an electrode which develops a localized field as a result of charge redistributions in the floating electrode, which are for example generated by voltages applied across adjacent bias electrodes. Thus, for example, as illustrated in FIG. 1, a floating electrode apparatus 10 can have a backing electrode 20, a non-conductive layer 30, a shielding electrode 60 and a floating electrode 70. In the illustrative floating electrode, a bias potential applied across the backing electrode and the shielding electrode (which two electrodes serve as the bias electrodes) causes a charge redistribution in the floating electrode to created the charged-particle attracting field at the floating electrode. Further description of floating electrodes and other forms of field generating devices for controlled field deposition can be found in U.S. application Ser. No. 08/661,210, filed Jun. 10, 1996, which document is incorporated herein by reference in its entirety. An advantage of floating electrode devices is that the amount of charged particles that will effectively adhere as a result of the field generated at the floating electrode depends on the size of the bias potential. (For more direct field generating apparatuses, the deposition can in principle continue for as long as a potential is applied.)

The field generating devices for controlled field deposition can be designed (a) to directly apply deposition material onto apparatuses that incorporate electrodes for generating the field or (b) for use with electrostatic chucks (i.e., field application structures) which operate in conjunction with the substrate on which deposition material is to be applied. In the former case (a), it is generally desirable that the metallization processes used to create the electrodes is susceptible to mass production techniques. For example, the metallization can be created by lithographic techniques where finely patterned electrodes are sought or by adhering or fusing metal layers to the substrate. In design (b), the electrostatic chuck is generally effective to electrostatically adhere the substrate to the chuck. This adherence of the substrate does not depend on the application of any process for creating a charge on the substrate, but instead is believed to be the result of a redistribution of charges in the substrate in response to the field generated by the electrostatic chuck. A third option is that the substrate is designed to reversibly couple with a device that provides the electrodes, such that the substrate and the coupled device provide a field-generating apparatus. In this way, the electrode structures that can be a source of manufacturing costs remain separate from the consumable on which reagents for conducting a chemical process will be deposited. In addition to the documents recited above, further information on electrode structures and electrostatic chucks can be found in U.S. application Ser. No. 08/630,012, filed Apr. 9, 1996, which document is incorporated herein by reference in its entirety.

The charge of the particles applied to a substrate can be generated for example by plasma treatment, radiation treatment (including treatment with suitably high energy electromagnetic radiation) or ion bombardment. More preferably, however, the charge is generated by tribocharging, wherein two materials with differing triboelectric constants rub against each other and transfer charge between one another. Tribocharging is more preferred over the enumerated charge-producing methods because it exposes the particles to the least amount of reaction-promoting energy, and hence the tribocharging method is less susceptible to causing compounds to degrade. Examples of materials that can be used for tribocharging include polytetrafluoroethylene ("TEFLON"), and polymers of chlorotrifluorethylene, chlorinated propylene, vinyl chloride, chlorinated ether, 4-chlorostyrene, 4-chloro-4-methoxy-styrene, sulfone, epichlorhydrin, styrene, ethylene, carbonate, ethylene vinyl acetate, methyl methacrylate, vinyl acetate, vinyl butyral, 2-vinyl pyridine styrene, nylon and ethylene oxide. See, for example, "Triboelectrification of Polymers" in K. C. Frisch and A. Patsis, *Electrical Properties of Polymers* (Technomic Publications, Westport, Conn.), which article is hereby incorporated by reference in its entirety. For example, polytetrafluoroethylene and polyethylene and other negatively charged materials will generally create a positive charge on an object. Nylon and other positively charged materials will generally create a negative charge on an object. Tribocharging and appliances for dispensing charged particles are describe in U.S. application Ser. Nos. 08/659,501 (filed Jun. 6, 1996) and 08/661,211 (filed Jun. 10, 1996). U.S. application Ser. No. 08/661,211 describes, in particular, an acoustic dispenser that uses vibratory energy and gating electric fields to dispense charged particles for deposition onto the substrate, and is incorporated herein by reference in its entirety.

In some embodiments, the charged particles may be made up of a wet toner wherein particles of liquid material or liquid material with suspended solids are charged. Charging of the liquid particles can be by, for example, tribocharging occurring at the time the particles are formed, utilizing contact potential differences between solid particles and the particles, or modifying the differences in electrical potential using surface treatments such as surfactants. (See, L. B. Schein, *Electrophotography and Development Physics,* Laplacian Press, 1996, p. 227.) Often it is favorable to dry deposit materials to avoid issues of solubility and stability of a chemical. On the other hand, however, liquid phase depositions are often practical, especially where cautionary procedures, such as limiting the time of exposure to the liquid phase and selecting appropriate carrier solvents, are employed.

2. Patterned Depositions and Removal of Excess Particles

Figure 2:
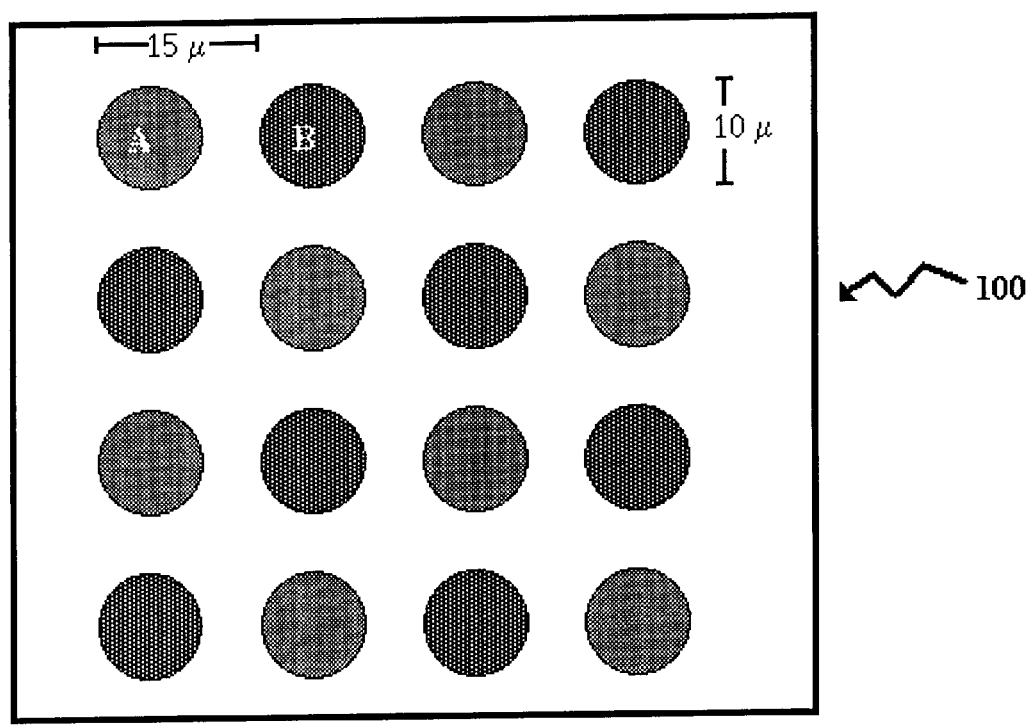
FIG. 2 shows a patterned deposition of material A and a material B.

Electrostatic or controlled field deposition methods can be used to apply patterns of materials on a substrate. For example, a pattern of an deposited material A and a deposited material B can be formed on a substrate 100 as illustrated in FIG. 2. In some embodiments of the invention, the deposition pattern can be highly dense, such as three hundred, six hundred or more dots per square inch (dpi). In preferred embodiments, the separation between the depositions is at least about 5 $\mu$m and the width of the depositions is at least about 10 $\mu$m.

After the deposition process, it is in some embodiments desirable to remove nonadherent particles. This removal process can be particularly important in embodiments where two separate patterns of deposition material are applied to a substrate, since remnants of a material A could possibly be found at the locations where a subsequent deposition of material B is anticipated. Methods to remove such nonadherent "background" particles can include rinsing (such as gentle rinsing with a sufficiently nonconductive and non-solubilizing solvent), blowing (such as gentle blowing with an inert gas), shaking, or application of an electronic brush. An electronic brush is any device that is or can be calibrated and positioned to apply an electronic field that applies a force on particles, where the field and resulting force can be manipulated mechanically or electrically to displace nonadherent charged particles.

Referring again to FIG. 2, suppose for example that the substrate 100 was conditioned to have a negative charge at the "A" sites by ion printing. After positively charged particles of A material are applied, those particles that are do not adhere are removed. Ion printing can then be applied to condition the "B" sites and apply the appropriate charged particles of B material. As discussed further below, additional layers can be applied to the substrate which can contain inert substances (inert to the use to which the substrate will be put), and these additional layers often can be applied without the need for patterned deposition or can be applied with reduced need for precise metering of the deposition amount. Accordingly, these layers often can be applied by methods other than electrostatic or controlled field deposition. For example, after the A material is deposited, the substrate is coated with layer of material to form an isolating layer, and thereafter the top layer of isolating material is conditioned by ion printing to receive the B material.

3. Creating Attached Molecules from Deposited Molecules

Typically molecules have been attached to solid supports by incubating solutions of the molecules with the support and allowing mass action to effect passive adsorptions to the support or covalent attachments with moieties on the support. In the present invention substantial quantities of material are coated onto a support, thereby increasing amount of material adjacent to potential reaction sites and increasing the efficiency of processes that attach the material to a support. The attaching processes can involve any physical force if the aggregate of the physical forces bonds a material (generally a compound) sufficiently to support the anticipated chemical process which is premised on such attachment. These physical forces include magnetic forces, electrical forces, gravitational forces, ionic bonding, hydrophobic effects, packing forces (such as van der Waals interactions) and covalent bonding.

Once material has been deposited on a solid support, the association between the deposited compounds and the support can mature to an attachment as that term has been defined herein without actively applying any further processing steps. However, in some instances, further processing can be desirable. Methods to increase the attachment between a deposited compound and the substrate can include:

(i) storing the coated solid support for a period of time sufficient to increase the strength of bonding between solid support and the deposited compound;

(ii) generating reactive moieties (such as for example free radicals) in a deposited compound or in the solid support that react to form a covalent attachment between the compound and the support;

(iii) providing a reactive moiety incorporated into the support at the surface and reacting the compound with the reactive moiety to covalently bond the compound to the surface;

(iv) maintaining a field that attracts the charged particles to the surface support for a period of time sufficient to increase the strength of bonding between solid support and the compound;

(v) wetting the coated surface with a liquid sufficiently to solubilize a portion of the deposited compounds, but preferably without adding enough liquid to elute deposited compound from the solid support; or (vi) heating the coated surface.

Item (ii) in the above listing recites a method of creating reactive moieties that cause crosslinking between a compound and the solid support. One of the most common means of accomplishing this crosslinking is to expose the coated solid support to ionizing radiation such as light or higher energy radiation to generate free radicals. This type of attachment has been utilized to couple nucleic acids to solid supports such as nylon filters (see, Ausubel et al., *Short Protocols in Molecular Biology,* Second Edition, John Wiley & Sons, 1992, pp. 2–29 to 2–30). In a related method, at least one of the compounds generates a reactive moiety when exposed to ionizing radiation. Exposure to reagents such as formaldehyde, glutaraldehyde and other crosslinking reagents (such as are described in Means and Feeney, *Chemical Modification of Proteins,* Holden-Day, 1971 and in the catalog produced by the Pierce Chemical Company, Rockford, Ill.) can also be used to generate crosslinks. Reactive substrates pursuant to item (iii) include for example substrates that incorporate photochemically reactive compounds.

As mentioned above, deposited materials become more tightly bound to the support with time. Where an electromagnetic attractive force remains in place to attract the charged particles of a deposition to a solid support, it is believed that packing processes will be accelerated, and that thereby the contact between the support and compounds in the deposited materials will increase. With such increased contact, the rate of formation of attachment bonds will increase. The attractive force can be a relatively high electric field, or a small force such as an image force.

The wetting process of item (v) allows for relatively large amounts of compound to be adjacent to the surface at which an attachment process is sought, while also gaining some of the benefits of solution processes for facilitating the interaction between the coated compound and the surface structure.

4. Washing

The solid support can be produced where the amount of a compound deposited is controlled to an amount less than that which the solid support can attach. In this case, then, there may be no need to act to assure that excess deposited compound is washed off of the solid support prior to using the solid support in a chemical process. Alternatively, the protocol used with the chemical process (for which the solid support is used) can be effective to wash away any non-adherent compound before such non-adherent compound has an opportunity to interfere with the efficiency of the chemical process. However, in some cases it is desirable to elute off weakly adhered compound prior to using the solid support in a chemical process. Conditions appropriate for such washing will vary depending on the properties of the solid support and of the compound (or compounds). The washing conditions can at a minimum include washing with at least one liquid with which the solid support will be contacted during the chemical process. To assure that only very tightly attached compounds are retained on the solid support, conditions can be selected that are more effective in extracting the compound than any to which the solid support will be exposed during the chemical process. However, these conditions should be such that adhered compound either retains or can recover the properties needed for the chemical process. For example, if a protein is adhered to the solid support such washing can include aqueous washings that include a detergent, such as a non-ionic detergent (for example, an alkylphenoxy-polyethylene oxide such as NP-40(Sigma Chemical Co., St. Louis, Mo.)). With many proteins and assays, the detergent used should only be a denaturing detergent if it is determined that the detergent-caused denaturation is reversible. (Note that in some cases it will not be important to the chemical process that the protein has retained its native conformation.)

5. Supports, Vessels and Well Trays

Supports can be solids having a degree of rigidity such as glass, porcelain, silicon, plastic, and the like. Support can also be flexible materials such as plastic or otherwise synthetic materials (such as nylon), materials made of natural polymers (such as cellulose or silk) or derivatives thereof (such as nitrocellulose) and the like. In certain embodiments the support is a porous material which can be rigid or flexible, such as sintered glass, intermeshed fibers including woven fabrics, and the like. In some embodiments, the solid support is a bead or pellet, which can be porous. In one embodiment where the support is a porous material the material of the support between depositions is fused. In this way, the substrate is porous at the portions where depositions have been made, but non-porous at intervening locations. The substrate thus has defined channels for allowing fluid flow through the substrate.

Figure 3A:
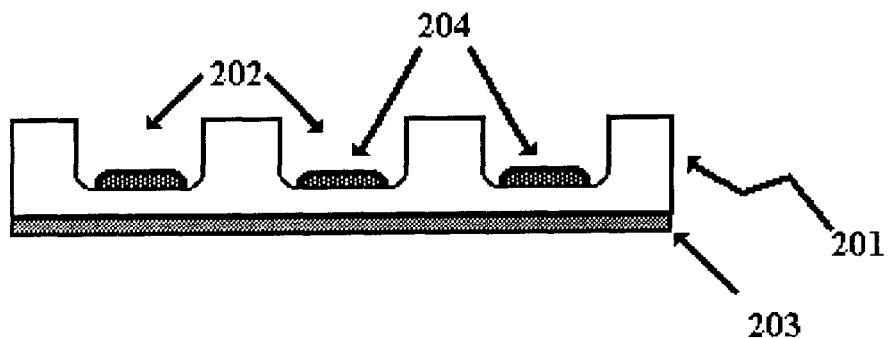
FIGS. 3A and 3B show a tray of wells in which materials have been deposited.
Figure 3B:
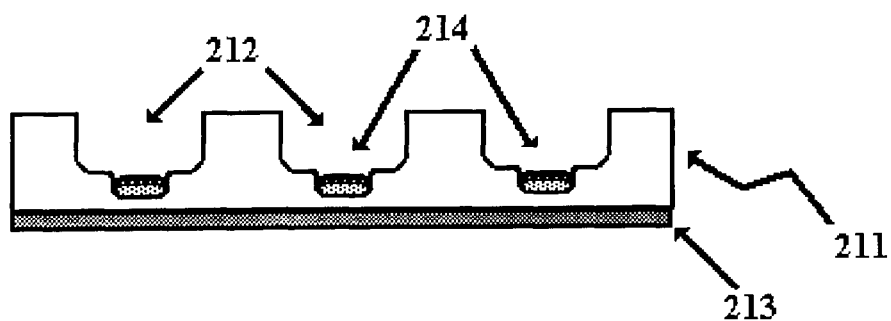

The substrate on which reagents are deposited or compounds are attached can form part of a vessel in which a chemical process is to be conducted. In particular, the substrate can be a tray of wells such as is formed by molding processes of plastic or is created by etching or laser drilling techniques in a variety of materials (as described, for example, in U.S. application Ser. No. 08/630,018, filed Apr. 9, 1996, which document is incorporated herein by reference in its entirety). Such vessels can have associated conductive layers which can form the electrodes used in controlled field deposition (where the conductive layer can for example couple with electrical leads which provide electrical potentials) or contribute a conductive layer supporting an image force to help retain charged particles. For example, FIGS. 3A and 3B illustrate substrates 201 and 211, which include wells 202 and wells 212, respectively. Deposited in the wells 202 and 212, are deposits 204 and 214, respectively. In FIG. 3B, the deposits 214 are found in indentations (not numbered) found at the bottom of wells 212. Underneath the wells 202 and 212 are conductive layers 203 and 213, respectively, which conductive layers can support an image force for retaining charged particles. In the illustration, the deposits 214 are made up of two layers, as indicated by a difference in shading.

In one embodiment of the invention, support reagents or attached compounds are added to the site at which the chemical process will occur in the form of a pellet or other carrier. For example, a pellet is added to each of a number of vessels, and liquid and sample materials are added to initiate the reaction process. In this case, the initial substrate on which the reagents are deposited is selected so that such pellets (or other carriers) can be built therefrom after the deposition process. Thus, for example, the initial substrate can be a tablet or a capsule (into which materials can be deposited). Alternatively, the initial substrate can be a sheet of material that can be cut into pellets or other carriers.

In certain embodiments, attached compounds or reagents are deposited on a membranes, paper, paper derivatives, or the like (hereinafter referred to as a flexible support). In these embodiments, the flexible support can be used to support a simplified chemical process, such as an assay that is initiated by dipping the flexible support in a fluid such as urine or another body fluid. Because electrostatic or controlled field deposition processes can create patterned depositions, in this embodiment (as well as any of the other deposition embodiments) compounds can be attached to the solid support in a pattern. For example, a deposition along a bar shape can be used to generate a color reaction if a positive control chemical process has occurred, while a second, intersecting bar shaped deposition can be used to generate a color reaction that is indicative of the experimental variable. Thus, for example a negative pregnancy test generates color at the first bar pattern ("–") and a positive result generates color at both of the intersecting bar patterns to form a "+" pattern.

The solid supports can include the styrene-divinylbenzene copolymerizate used by Merrifield when he introduced solid phase peptide synthetic techniques. Merrifield, *J. Am. Chem. Soc.* 85: 2149, 1963. See, also Barany et al., "Recent Advances in Solid-Phase Synthesis," in *Innovation and Perspectives in Solid Phase Synthesis: Peptides, Polypeptides, and Oligonucleotides,* Roger Epton, Ed., collected papers of the 2nd International Symposium, Aug. 27–31 1991, Canterbury, England, p. 29. These supports are typically derivatized to provide a "handle" to which the first building block of an anticipated product can be reversibly attached. In the peptide synthesis area, suitable supports include a p-alkoyxbenzyl alcohol resin ("Wang" or PAM resin) available from Bachem Bioscience, Inc., King of Prussia, Pa.), substituted 2-chlorotrityl resins available from Advanced Chemtech, Louisville, Ky., and polyethylene glycol grafted poly styrene resins (PEG-PS resins) are available from PerSeptive Biosystems, Framingham, Mass. or under the tradename TentaGel, from Rapp Polymere, Germany. Similar solid phase supports, such as polystyrene beads, are also used with oligonucleotides by the phosphotriester approach. See Dhristodoulou, "Oligonucleotide Synthesis: Phosphotriester Approach," in *Protocols for Oligonucleotide Conjugates,* S. Agrawal, Ed., Humana Press, N.J., 1994; Beaucage, "Oligodeoxynucleotide Synthesis: Phosphoramidite Approach," in *Protocols for Oligonucleotide Conjugates,* S. Agrawal, Ed., Humana Press, N.J., 1994;

Froehler, Oligodeoxynucleotide Synthesis: H-Posonate Approach," in *Protocols for Oligonucleotide Conjugates*, S. Agrawal, Ed., Humana Press, N.J., 1994; Damha and Ogilvie, Oligodeoxynucleotide Synthesis: "Silyl-Phosphoramidite Method," in *Protocols for Oligonucleotide Conjugates*, S. Agrawal, Ed., Humana Press, N.J., 1994. Suitable supports for oligonucleotides further include the controlled pore glass (cpg) and polystyrene supports available from Applied Biosystems, Foster City, Calif. The solid supports of use in the invention can further include the beads sold by Polymer Laboratories, Amhearst, Mass. Desirable reactive site functionalities include without limitation halogen, alcohol, amine and carboxylic acid groups.

Another option for creating a solid support with reactive sites is to directly derivatize the solid support so that it can be coupled to a compound. The chemistry used to do this can be the same or similar to that used to derivatize controlled pore glass (cpg) beads and polymer beads. Typically, the first step in this process is to create hydroxyl groups (if they do not already exist on the support) or amino groups on the support. If hydroxyl groups exist or are created, they are typically converted to amino groups, for instance by reacting them with gamma-aminopropyl triethoxy silane. Flexible tethers can be added to the amino groups with cyclic acid anhydrides, reactions with polymerized alkylene oxides and other methods known to the art. Examples of such methods are described in Fields et al., "Synthetic Peptides: A User's Guide," W. H. Freeman and Co., Salt Lake City, Utah, 1991.

Methods of creating reactive sites include, particularly for the case where the solid support is made of plastic, exposing the solid support to a reactive plasma, such as that created by a glow-discharge in the presence of ammonia or water, to create $NH_2$ groups. Such procedures are described in "Modification of Polymers," Carraher and Tsuda, eds., American Chem. Soc., Washington, D.C., 1980. Another method, particularly useful with glass, ceramic or polymeric substrates, is depositing a film of silicon monoxide by vapor deposition at low temperature to create hydroxyl functionalities. Glass surfaces can be treated with alkali, for instance with KOH or NaOH solutions in water or water/alcohol mixtures, to expose hydroxyl functional groups.

Non-annealed borosilicate glass surfaces, including coatings of non-annealed borosilicate glass created by chemical vapor deposition, can be etched, for instance with hydrofluoric acid dissolved in water, to dissolve the regions that are rich in boron, which process creates a porous structure with a large surface area. This porous structure can be treated with alkali to expose hydroxyl groups.

Another method to increase the reactive surface area of a solid support is to create columnar structures of silicon monoxide, for instance by thermal evaporation of $SiO_x$. Another such method is to insert into the reaction cells fabrics, such as non-woven glass or plastic (preferably fiberglass or polypropylene fiber) fabrics and plasma treating the fabric to create reactive sites. Still another method uses spin-on glass, which creates a thin film of nearly stoichiometric $SiO_2$ from a sil-sesquioxane ladder polymer structure by thermal oxidation. Sol-gel processing creates thin films of glass-like composition from organometallic starting materials by first forming a polymeric organometallic structure in mixed alcohol plus water and then careful drying and baking. When the sol-gel system is dried above the critical temperature and pressure of the solution, an aerogel results. Aerogels have chemical compositions that are similar to glasses (e.g. $SiO_2$) but have extremely porous microstructures. Their densities are comparably low, in some cases having only about one to about three percent solid composition, the balance being air.

6. Alternative Methods of Applying Coatings

Additional layers can be applied to the substrate without electrostatic or controlled field deposition techniques. For example, coating materials, which can be dry or more preferably dissolved or suspended in a volatile carrier, are applied by spraying, brushing, dipping or the like. For dry powder depositions it will often prove desirable to mechanically scrap the top of the applied material assure that a uniform thickness of material has been applied. The coating material may for example contain a low melting point polymer such as a polyethylene glycol which is fused with moderate heat to more strongly bond the applied layer of coating material to the substrate. Alternatively, sheets of material are applied for example using an intermediate adhesive or, where the materials are suitable, fusion bonding. Fusion bonding techniques include heat fusion, ultrasonic fusion, laser fusion, pressure bonding, and the like.

In some embodiments, the additional layers dissolve in the liquid of the anticipated subsequent chemical process.

7. Controlled Release

As an aspect of the invention, a reagent can be deposited such that its release does not occur until after a time delay or until after a change of conditions, such as a pH change, has occurred. In one form of the invention, the controlled release operates to delay the operative phase of a chemical process until all of the sites at which the process is to be conducted in parallel have been fully formulated. For example, liquid can be added to all of the sites, and then at least a subset of sites receives material from unknown samples or control samples. In one case, the simple addition of the liquid initiates a window time during which to add all of the unknown or control material, after which time window various reagents that support the chemical process are released into the liquid. Alternatively, a simple triggering event like a change of pH could begin the release of the process-supporting reagents. Also, multiple layers of materials can be used so that, for example, a first deposited layer provides reagents that support a first chemical process, and thereafter another deposited layer releases reagents that support a second chemical process. Such layered release layers can provide for two, three, or more phases of a chemical process.

Substantial development has been made, particularly with reference to pharmaceuticals, in the field of controlled release or sustained release compositions. These compositions tend to be made up of mixtures of polymers with varying swelling properties and various excipients. Some of these compositions are designed with a focus on minimizing swelling in an acidic environment such as that of the human stomach, while allowing faster swelling in an alkali environment, such as that of the small intestines. Particularly for veterinary applications, the pH dependence of the swelling profile can be reversed to favor swelling, and thereby dissolution of the active components of the composition, in acidic environments.

Examples of controlled release technology can be found in: (1) U.S. Pat. No. 4,012,498, "Sustained Release Formulations," Kornblum et al., Sandoz, Inc. (contains alkaloids incorporated into a basic pH affected controlled release matrix selected from cellulose acetate phthalate, polyvinyl acetate phthalate and hydroxy propylmethyl cellulose phthalate); (2) U.S. Pat. No. 4,111,202, "Osmotic System for the Controlled and Delivery of Agent Over Time," Feliz, Alza Corp.; (3) U.S. Pat. No. 4,173,626, "Sustained Release Indomethacin," Dempski et al., Merck & Co., Inc. (coats pellets with polyvinyl acetate to slow release); (4) U.S. Pat. No. 4,178,361 "Sustained Release Pharmaceutical Composition," Cohen et al., Union Corp. (uses a water-soluble but water swellable matrix which holds a biological binding agent); (5) U.S. Pat. No. 4,221,778, "Prolonged Release Pharmaceutical Preparations," Raghunathan, Pennwalt Corp. (ion exchange resin particles with drug absorbed thereon which are treated with an impregnating agent [polyethylene glycol, propylene glycol, mannitol, lactose and methylcellulose] to slow swelling in water and coated with a diffusion barrier); (6) U.S. Pat. No. 4,248,857, "Sustained Release Pharmaceutical Compositions," DeNeale et al., American Home Products Corp.; (7) U.S. Pat. No. 4,252,786, "Controlled Release Tablet," Weiss et al., E. R. Squib & Sons, Inc. (medicament compressed with a blend of polymeric vinyl pyrrolidone and a caroxyvinyl hydrophilic polymer and coated with a substantially water insoluble, but water permeable film); (8) U.S. Pat. No. 4,259,314, "Method and Composition for the Preparation of Controlled Long-Acting Pharmaceuticals," Lowey; (9) U.S. Pat. No. 4,293,539, "Controlled Release Formulations and Method of Treatment," Ludwig et al., Eli Lilly and Company (active dispersed in a copolymer of glycolic acid and lactic acid); (10) U.S. Pat. No. 4,309,404, "Sustained Release Pharmaceutical Compositions," DeNeale et al., American Home Products, Corp.; (11) U.S. Pat. No. 4,309,405, "Sustained Release Pharmaceutical Compositions," Guley et al., American Home Products, Corp.; (12) U.S. Pat. No. 4,505,890, "Controlled Release Formulation and Method," Jain et al., E. R. Squib & Sons, Inc. (a coated core containing a hydrocolloid gelling agent [methyl cellulose, hydroxypropyl cellulose, hydroxy ethyl cellulose, sodium carboxymethyl cellulose or mixtures thereof]; (13) U.S. Pat. No. 4,587,118, "Dry Sustained Release Theophylline Oral Formulation," Hsiao, Key Pharmaceuticals, Inc., (seed coated with theophylline and polyvinylpyrrolidone, then coated with a mixture of ethylcellulose and hydroxypropylcellulose); (14) U.S. Pat. No. 4,666,705, "Controlled Release Formulation," DeCrosta et al., E. R. Squib & Sons, Inc.; (15) U.S. Pat. No. 4,716,041, "Diffusion Coated Multiple-Units Dosage Form," Kjornaes et al., A/S Alfred Benzon (formulation is heated to form, in an film coating located inside an outer film layer, a continuous phase); (16) U.S. Pat. No. 4,784,858, "Controlled Release Tablet," Ventouras, Zyma SA (core contains water soluble agent, a water-insoluble polymeric excipient [e.g. polyvinylchloride or polymer of lower alky acrylates or methacrylates], and a water-insoluble substance that swells on contacting water, and core is coated with a elastic, water-insoluble, semipermeable diffusion coating); (17) U.S. Pat. No. 4,917,900, "Controlled Release Formulations Containing Zidovudine," Jones et al., Burroughs Wellcome Co. (coated with a mixture of a polymer of alkyl esters of acrylic or methacrylate and ethyl cellulose); (18) U.S. Pat. No. 4,973,469, "Drug Delivery System," Mulligan et al., Elan Corp., PLC (active ingredient and an inert substance whose aqueous solubility is inversely proportional to that of the active are adsobed to a cross-linked polymer such as cross-linked polyvinylpyrrolidone, carboxymethylcellulose or methylcellulose); (19) U.S. Pat. No. 5,178,868, "Dosage Form," Malmqvist-Granlund et al., Kabi Pharmacia Aktiebolaq (cores coated with a mixture of (a) a copolymer of vinyl chloride/vinyl acetate/vinyl alcohol monomers and (b), for creating pores, a substance that is soluble in water); (20) U.S. Pat. No. 5,234,691, "Sustained-Release Preparation of Basic Medicinal Agent Hydrochloride," Uemura et al., Sumitomo Pharmaceuticals, Co., Ltd. (granules containing basic agent and a polyanion such a carboxyvinyl polymer or carboxymethcellulose and coated with a slightly water-soluble macromolecular substance such as polyvinyl acetate, ethyl cellulose, aminoalkylmethacrylate copolymer, methacrylic acid copolymer, cellulose acetates, polyethylene, polymethyl methacrylate, polydimethyl-siloxane, hardened oil, beeswax, carnauba wax, sucrose fatty acid ester, sorbitan monostearate, glyceryl monostearate, glyceryl monomyristate, glyceryl distearate, stearic acid, stearyl alcohol, and mixtures thereof); (21) U.S. Pat. No. 5,286,493, "Stabilized Controlled Release Formulations Having Acrylic Polymer Coating," Oshlack et al., Euroceltique, S. A. ((a) coating a substrate with a plasticized aqueous dispersion of ammonio methacrylate copolymers which are copolymerizates of acrylic and methacrylic esters, having a low content of quaternary ammonium groups acrylic and methacrylic acid esters, having a permeability which is unaffected by the pH conditions prevailing in the gastrointestinal tract, and (b) curing the coated substrate with a temperature greater than the glass transition temperature of the aqueous dispersion); (22) U.S. Pat. No. 5,472,712, "Controlled-Release Formulations Coated with Aqueous Dispersions of Ethylcellulose," Oshlack et al., Euroceltique, S. A.; (23) U.S. Pat. No. 5,492,700, "Process and Composition for the Development of Controlled Release Gemfibrozil Dosage Form," Ghebre-Sellassie et al., Warner-Lambert Co. (a single granulation of gemfibrozil particles granulated with a release-control agent such as of cellulose phthalate, ethyl cellulose, polyvinyl phthalate, cellulose succinate, cellulose buryrate, poly(meth)acrylic acid, partially esterified poly(meth)acrylic acid and mixtures thereof); (24) U.S. Pat. No. 5,580,578, "Controlled Release Formulations Coated with Aqueous Dispersions of Acrylic Polymers" Oshlack et al., Euroceltique, S. A.; (25) U.S. Pat. No. 5,643,602, "Oral Composition for the Treatment of Inflammatory Bowel," Ulmius, Astra Aktiebolag (a seed with a first coating of film-forming, water-soluble or insoluble polymers and a second coating of a membrane containing a pharmaceutically acceptable, film-forming, anionic carboxylic polymer which is difficult to dissolve at a low pH but is soluble at a higher pH of about 4 to 7.5); (26) U.S. Pat. No. 5,656,295, "Controlled Release Oxycodone Compositions," Oshlack et al., Euroceltique, S. A, and (27) Ishikawa et al., Chem. Pharm. Bull. 43: 2215–20, 1995 (describing polybenzylmethacrylate copolymer having a cross-linkable part on the side chain for use as an outer layer in a controlled-release formulation, which copolymer is crosslinked for example by contacting an oxygen plasma).

One focus of controlled release technology is in coating or mixing compounds of interest with compositions that swell a given type of liquid at a predictable rate. This technology relies substantially on the swelling properties of polymers. Where one seeks to reduce the swelling rate in acidic aqueous environments, often the polymers used include acid functional groups that titrate between a low solubility acid form and a higher solubility salt form. Where one seeks to reduce the swelling rate in basic aqueous environments, often the polymers used include base functional groups that titrate between a low solubility base form and a higher solubility salt form. It should be noted that the excipients or fillers can play a role in modulating the rate at which the controlled release composition swells.

Additionally, the components of a controlled release formulation which will have an active role in a subsequent chemical process can affect the dissolution profile, as will be recognized by those of ordinary skill. The effects of these "actives" on the swelling profile can generally be expected to be greater if admixed with the controlled release composition rather than deposited under a layer of controlled release composition.

The pH sensitivity of certain controlled release compositions can be utilized in designing protocols for chemical processes. For example, if a first process is to occur at a low pH and a subsequent process at a higher pH, the reagents that support the second process can be sequestered by a controlled release composition that is more resistant to swelling in an acidic environment.

Figure 4:
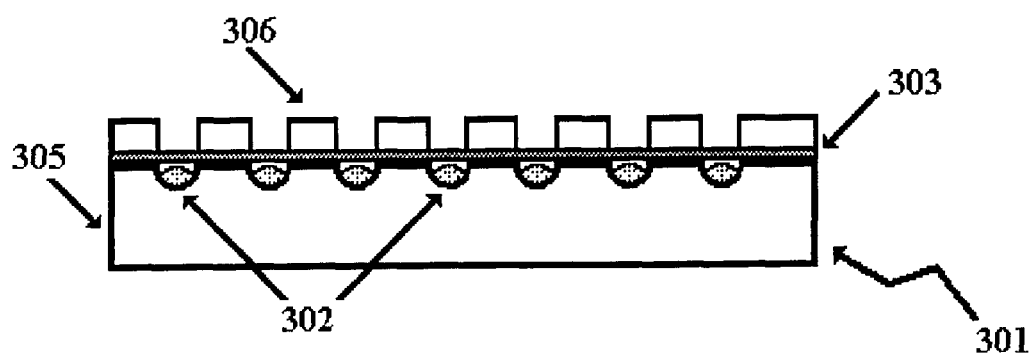
FIG. 4 shows a substrate with controlled release features.

Another mechanism for controlling release is to provide a kinetic/diffusion barrier to substrate deposited chemicals passing into a liquid. For example, FIG. 4 illustrates a substrate 301 in which materials have been deposited in cavities 302, which in turn is covered by a membrane 303. The substrate is made up of a lower portion 305, to which is fused an upper portion 306. The upper portion defines wells above the locations of the cavities. This diffusion control mechanism can of course be combined with the rate-of-swelling mechanism discussed above. As alluded to above in the recitation of published examples of controlled release formulations, the diffusion control can be formed as polymer-containing films overlying an interior composition.

8. Methods and Substrates for Handling Incompatible Reagents

In many cases reagents that are used together in a chemical process are not stable if stored together, especially in solution. This lack of stability (at least in the long term) is often attenuated when reagents are stored in a solid form such that opportunities for the reagents to collide are minimized. By the present invention, the reagents can be deposited by a dry deposition method or, if liquids are used in the deposition process, the time during which the reagents are solubilized or suspended in the liquids can be kept to a minimum. Using the intermediary layers described above, and even intervening layers of controlled release compositions, the incompatible reagents can be further separated. By simply depositing the reagents in separate deposition steps, the exposure of the reagents to one another is reduced even where the incompatible reagents are deposited in adjacent layers.

Reagents can be incompatible in the sense that one is favorably processed in a liquid in which a second reagent is insoluble or unstable. This contingency can be addressed by the present invention by having the reagents both applied by a dry deposition method, or by having the second reagent applied by a dry deposition method.

9. Avoiding Unacceptable Levels of Adsorption to the Substrate

In certain embodiments of the invention, materials are deposited onto solid supports in a form that can be solubilized and removed from the solid support. However, as discussed above, where depositions are made directly on a substrate material (which for example is not soluble in a liquid to which the substrate will later be exposed), at least an amount of the deposited material can be expected to be attached to the substrate material. This effect will very with the degree to which the substrate material tends to attach to substances found in the deposited material. In many instances the amount of attached material will be small compared with the amount of material that can later be dissolved during the course of a chemical process, and the percentage amount attached will be sufficiently reproducible so that the practical effect on the subsequent chemical process is negligible. However, these adsorption effects can be further minimized by coating the substrate with a soluble material, and then applying the deposition material over this initial coating.

In certain embodiments, it is desirable to have certain compounds attached to the substrate, and other compounds, which may be present in an overlaid coating, applied in a form that can be solubilized. For example, each well in a reaction tray can have attached to its bottom surface a macromolecule involved in an assay (such as an antibody, other receptor molecule, or a nucleic acid probe). A cocktail of the reagents needed for at least the first step of an assay involving the macromolecule can also be applied to a surface of the well, so that the addition of a solubilizing liquid provides a substantial beginning for the assay.

B. Polymer Depositions, in Particular Capture Reagent Depositions

In a great number of chemical processes such as assays the process depends on having attached to a solid support a polymer such as a polypeptide (including proteins, polypeptides and peptides) or a nucleic acid. These polymers often serve as "capture" reagents. For example, immunological assays use antibodies (or recombinant analogs thereof) bound to a solid support, where the antibodies serve in many cases to bind (i.e., "capture") a substance that is the target of the assay. Such immunological assays are described for example in Ausubel et al., *Short Protocols in Molecular Biology,* Second Edition, John Wiley & Sons, 1992, pages 11-1 to 11–54, which text is incorporated herein by reference. Nucleic acids are often bonded to solid supports and used to capture nucleic acids of complementary sequence. Examples of such techniques are described for example in Ausubel et al., *Short Protocols in Molecular Biology,* Second Edition, John Wiley & Sons, 1992, Unit 2 (Preparation and Analysis of DNA), Unit 4 (Preparation and Analysis of RNA), Unit 6 (Screening Recombinant DNA Libraries) and Unit 15 (The Polymerase Chain Reaction), which text is incorporated herein by reference.

With the methods of making solid supports described herein combinations of polymers (such as macromolecules) can be bound to the solid support in well-characterized ratios. The methods herein are also more amenable to automation than previously used methods such as passive adsorption upon incubation with a solution, blotting or ultrafiltration onto a membrane optionally followed by a process such as UV crosslinking, and a liquid/solid phase reaction with a crosslinking moiety on the solid support. With the methods of the invention, it is believed that high yield of attached polymers can be achieved, that the attached polymers have excellent stability, and that the attachment methodology can be used to enhance the percentage of attached polymers that maintain native structures needed in some chemical processes.

In preferred deposition methods according to the invention, the polymers are deposited in dry form. Thus, an initial step is to isolate the polymers in dry form (unless for example it is obtained from a synthesis procedure in dry form). With many polymers, this isolation step can be conducted by precipitating the polymers, such as precipitating with acid, salt, or organic solvents (such as ethanol), followed with a further drying process. With proteins it is often desirable to isolate a dry form by lyophilization, since this method tends to better preserve the native structure of the dried protein. It should be understood that a dry form of a molecule is simply a form that can be handled as a solid. Lyophilized proteins generally contain bound solvent molecules, and the crystal or other precipitated form of many compounds incorporate solvent molecules.

C. Probe Arrays

The invention provides the ability to deposit probes in a spatially resolved manner, as discussed above. Thus, for example, dense patterns of attached compounds can be deposited on a solid support (see FIG. 2 for a relatively simple pattern). In this way, arrays of "probes" such as antibodies or nucleic acids can be deposited on a solid support. The array can include positive control probes designed to generate a positive result with the material that is to be subjected to the chemical process, as well as negative control probes that ordinarily should not generate a positive result. The array can further include an variety of probes. For example, the array can include a variety of antibodies against compounds such as markers for the presence of microbes (such as disease-causing microbes) or a variety of nucleic acid probes that hybridize with nucleic acids such as nucleic acids derived from microbes.

Fodor et al. have described techniques for preparing spatially resolved nucleic acid probe arrays such as can be achieved by the present invention by using photosensitive protecting groups and masks during a synthesis performed on a solid support. See, for example, Fodor et al., WO 92/10092, published Jun. 25, 1992 or Fodor et al., *Nature* 364: 555–556, 1993. With the present technique, however, processing is simplified and, it is believed, can be accomplished on a shorter time scale.

Figure 5:
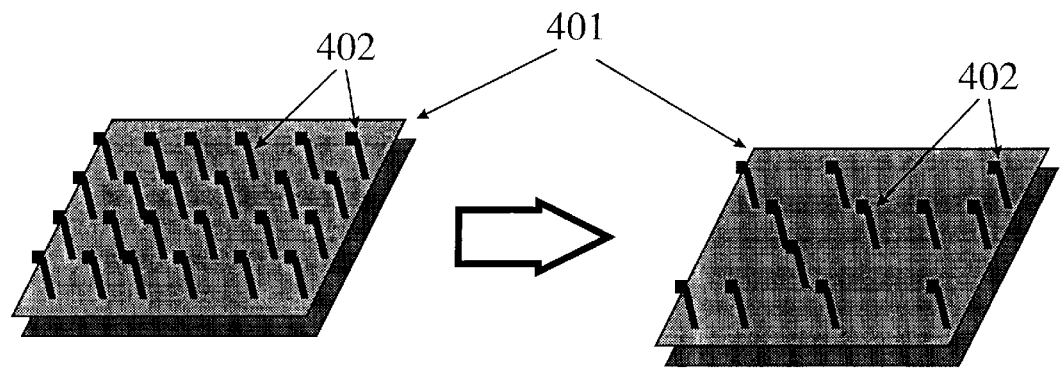
FIG. 5 presents an illustration of a nuclease protection assay using a solid support prepared according to the invention.

FIG. 5 illustrates an example where a support 401 has attached thereto a number of probes 402, which do not have to be the same. In the illustration the probes 402 incorporate a detectable label such as radioactivity or fluorescent moiety. After incubation with a nucleic acid-containing sample and application of a nuclease, only those probes that sufficiently anneal with nucleic acids in the sample are in a double-stranded form that resists digestion with a nuclease (which is single strand specific). Examples of protocols used in nuclease protection assays with the nucleases S1 (an endonuclease specific for single strands) and Ribonuclease A (an endoribonuclease used under salt conditions that make it specific for single-stranded RNA) can be found in Ausubel et al., *Short Protocols in Molecular Biology,* Second Edition, John Wiley & Sons 1992, pp. 4–14 to 4–21, which text is incorporated herein by reference. Similar assays can be conducted with, for example, exonucleases under conditions such as those described in Ausubel et al., *Short Protocols in Molecular Biology,* Second Edition, John Wiley & Sons, 1992, Unit 3, which text is incorporated herein by reference.

D. Nucleic Acid Amplification Devices and Protocols

In certain embodiments of the invention the solid support is set up preferably using the deposition methods of the invention to have reagents needed in a nucleic acid amplification method. Such methods include without limitation (1) Polymerase chain reaction (PCR; see, e.g., U.S. Pat. No. 4,683,202 and *Short Protocols In Molecular Biology* (Frederick M. Ausubel et al., eds. 1992)(hereinafter, Ausubel et al.), Unit 15.1); (2) ligase chain reaction (LCR; see, e.g., European Patent Publication 320,308 and Schachter et al.,*J. Clin. Microbiol.,* 32, 2540–2543 (1994)); (3) strand displacement amplification (SDA; see, e.g., Walker et al., *PCR Methods and Applications,* 3, 1–6 (1993)); (4) nucleic acid sequence-based amplification (NASBA; see, e.g., van Gemen et al., *J. Virol. Methods,* 43, 177–188 (1993)); and (5) transcription-mediated amplification (TMA; Pfyffer et al., *J. Clin. Micro.,* 34, 834–841 (1996)). The procedures for these amplification methods are described for example in the above-cited documents, and this description of methodology is incorporated by reference in the present disclosure. Amplification methods generally use at least one and typically two "primers," which are relatively short (e.g. 15 to 25 nucleotides) and can anneal (i.e., base pair) with a target nucleic acid to provide a starting point for the action of an enzyme (such as an enzyme which an organism uses for example to replicate or maintain nucleic acid). Thus, a nucleic acid polymerase starts from one of the primers to create from nucleotide triphosphate building blocks a strand that is "complementary" to at least a portion of the strand to which the primer has annealed. Or, in another example, a DNA ligase joins two primers if they anneal to the target nucleic acid in an appropriate juxtaposition for ligation.

The first two amplification methods, PCR and LCR, both relate to amplification of DNA segments, and are commonly used in methods of detection and analysis of such segments. These amplifications commonly are conducted using thermal cyclers for generating a cycles of denaturing-renaturing/reaction temperatures for the reaction. SDA and NASBA can be used to amplify a DNA segment, though SDA provides DNA products while NASBA provides RNA amplification products. Typically, these amplification methods require at least an initial high temperature incubation to provide for the denaturing of the target DNA upon or prior to the adding of primer, after which the reactions are conducted isothermally at a lesser temperature. For example, NASBA includes an initial incubation at 75° C. followed by incubations at 41° C. Similarly, SDA includes an initial incubation at 95° C. followed by incubations at 37° C.

1. Solid Supports for Nucleic Acid Amplification

The solid supports of this aspect of the invention have (1) deposited thereon one or more reagents that support an amplification reaction [such as an enzyme, buffering system, salts, primers, stabilizers (such as sucrose or other sugars, carbohydrates or other inert polymers) and the like] or (2) deposited and attached at least one primer. The invention thereby provides a manufacturing process to deposit consumables at the sites where amplification reactions are to occur. Standardized manufacturing processes in turn reduce the susceptibility of an amplification method to error caused by inaccuracies in dispensing consumables to the reaction sites.

The deposition methods of the invention allow for depositing reagents for amplifications that can occur in very small volumes. With the resulting scaling down, the device in which the amplification is conducted can have a low thermal impedance, so that the ramp times for heating and cooling cycles are shortened. Additionally, if for example the thermoelectric heat pumps described in U.S. application Ser. No. 60/010,513, filed Jan. 24, 1996 and U.S. application Ser. No. 08/786,956, filed Jan. 23, 1997 are used, rapid temperature transitions both upwards and downwards can be achieved (these patent applications are incorporated herein by reference in their entirety). Such rapid temperature transitions decrease the cycling time (for example to less than five minutes per cycle) and assure for example that the reaction mixtures are only minimally exposed to intermediate temperatures that can allow an enzyme such as DNA polymerase to be active, but with reduced fidelity.

By systematically applying primers on a solid support for an amplification reaction, the relative location and identity of each kind of primer is established, and is not susceptible to certain identification errors in the hands of a laboratory worker.

2. Method of Amplification with at Least One Probe Attached

The invention also provides a method of conducting a nucleic acid amplification reaction where at least one probe is attached to the solid support. For any particular amplification requiring two primers it is preferred that one be attached to the support and the other be in the solution phase. Preferably, the detection method employed seeks to identify a signal that is attached to the solid support after the amplification process (examples of such detection methods are set forth below). The invention allows for multiple amplifications to be conducted using a single mixture of reagents, while allowing each individual amplification outcome for the mixture be identifiable due to the spatial separation of the separate attached primers.

In such mixed-but-spatially-resolved amplifications it is desirable to have the process occur under conditions that minimize the diffusion of second strand amplification products (those that are not attached to the solid support via the attached primer) during strand melting steps of the amplification process. This diffusion limitation helps assure that the second strand is available locally at the site of the matching attached primer so that logarithmic amplification can occur. Note, however, that in contexts where arithmetic amplification is acceptable, there is either no need or reduced need to localize the second strand product. The second strand product can be localized for example by maintaining a relatively thin layer of liquid of the reaction mixture (see for example the reaction chamber described in U.S. application Ser. No. 60/010,513, filed Jan. 24, 1996 and U.S. application Ser. No. 08/786,956, filed Jan. 23, 1997), adding viscosity enhancing substances to the reaction mixture, and taking care not to agitate the reaction mixture during temperature cycling steps.

The attached primer can be labeled for example by incorporating radioactive isotopes or by attaching a detectable reagent such as a fluorescent molecule. If labeled with an attached detectable reagent, it is preferable that the reagent be attached in a manner that is susceptible to being removed from the solid support by the action of an endonuclease. Suitable chemistries are described in Holland et al., *Proc. Natl. Acad. Sci. USA* 88: 7276–7280, 1991. With the label attached to the primer that is attached to the solid support, detection can involve the application of a nuclease that digests away the label that is not protected by a double-stranded interaction with an amplified nucleic acid.

Alternatively, the label can be incorporated into the second primer involved in an amplification. In this way, spatially resolved association of the labeled primer with the solid support occurs through hybridizations that are mediated by amplified sequences.

E. Apparatus for Chemical Processes Conducted on a Solid Support, Such as for Nucleic Acid Amplifications The invention further provides a device for conducting chemical processes on a solid support (especially nucleic acid amplifications) comprising:

a bracket for bracing together at least two layers of materials which comprise:
  a first layer of one or more releasable containers of liquid for supporting a chemical process that uses a sample that prospectively contains a target molecule which generates a responsive result in the chemical process; and
  a second layer of a first porous material on which are attached molecules of the samples, which molecules prospectively include target molecules,
wherein the liquid from the containers can be released from the containers to bath the first porous material. In a particularly preferred embodiment, the device comprises:

a bracket for bracing together at least two layers of materials which comprise:
  a first layer of one or more releasable containers of liquid for supporting a nucleic acid amplification reaction with a sample that prospectively contains a target nucleic acid from which a amplicon nucleic acid can be amplified as specified by amplification primers; and
  a second layer of a first porous material on which are attached the nucleic acids of samples, which nucleic acids prospectively contain target nucleic acids,
wherein the liquid from the containers can be released from the containers to bath the first porous material.

Preferably, the first porous material contains a pattern of applications of materials that prospectively contain target nucleic acids. The first porous material includes a membrane, which membrane or film can be without limitation any of those that have been used to attach nucleic acids such as nylon or nitrocellulose.

In a preferred embodiment, the bracket further braces between the first and second layers a third layer of a second porous material. Preferably, on or in the second porous material there are deposited one or more reagents for supporting the chemical process (such as a nucleic acid amplification), which reagents are preferably in dry form. In one preferred embodiment, the reagents are deposited in a pattern matching the pattern of prospective target molecule depositions. Preferably, the second porous material is embossed or otherwise non-porous in regions separating porous regions on or in which the reagents optionally are deposited. The non-porous regions serve to create channels directing liquid from each release container through the second porous material to a region of the first porous material that aligns with the release container. The second porous material is a material that can support deposited reagents in a dry form and can be, for example, a membrane or film or a woven or non-woven mesh of fibers (such as a cellulosic material, a glass fiber material), a gelatin, a synthetic gel such as an acrylamide gel, or a more rigid porous material [such as sintered glass, porous polymer material (such as porous polycarbonate)].

Figure 6:
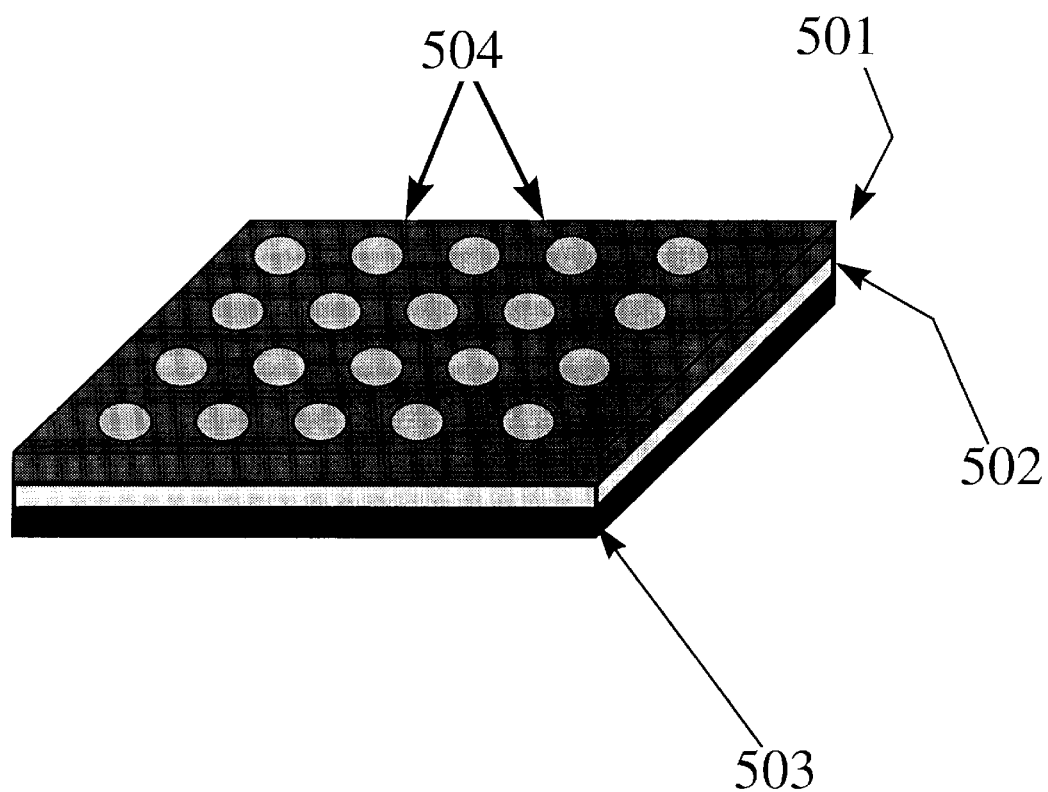
FIG. 6 shows three layers braced together as part of an apparatus for conducting chemical processes.

FIG. 6 shows a sandwich structure of three layers according to the invention. First layer 501 contains the release containers 504. The release containers can for example be sealed with plastic undercovers that burst open upon application of pressure to the top of layer 501. The invention also contemplates a device for uniformly applying pressure to the top of layer 501 to thereby open the release containers. Porous third layer 502 receives the liquid released from the release containers. If the third layer incorporates dry forms of reagents for a chemical process, the liquid from the release containers dissolves them and blots them onto the porous first layer 503.

Typically, the first layer 503 is removed from the sandwiching device after it has been bathed in reagents and liquid, and placed in a temperature control apparatus. For example, in a hybridization reaction the porous first layer with bathing liquid from the release reservoirs is incubated at elevated temperature. In amplification reactions, the porous first layer with bathing liquid from the release reservoirs is generally subjected to a temperature cycling reaction. In antibody binding or other binding assays, elevated temperature may not be required, and in some cases reduced temperatures are often applied.

In one preferred embodiment, the liquids of releasable containers is made up of water, stable additives such as sucrose, glycerol, or other alcohol, stable buffering agents such as phosphate salts, other stable salts, and other components that are stable in aqueous solution without a need for refrigeration. The second porous material preferably has deposited on it components that are more stable in a dry form, such as nucleotide (including deoxynucleotide) triphosphates and enzymes. Primers are generally stable in solution, but are more preferably found in a dry form such as deposited at the second porous material or on the first porous material. Examples of release containers include the Bursapak supply chambers described in U.S. application Ser. No. 08/786,956, filed Jan. 23, 1997, which application is incorporated herein in its entirety.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A solid support having a surface with a composition of at least one polymer dry deposited thereon by electrostatic or controlled field deposition, wherein the polymer is a nucleic acid, a peptide, or a protein and is attached to the surface, wherein electrostatic deposition comprises forming an electrostatic charge on the surface effective to attract charged particles containing the composition to the surface, and controlled field deposition comprises forming an electromagnetic field effective to direct such charged particles to the surface.

2. The solid support of claim 1, wherein the solid support is a flexible support.

3. A method of preparing a solid support having a surface with a composition of at least one polymer, wherein the polymer is a nucleic acid, a peptide, or a protein and wherein the polymer is attached to the support comprising:

creating an electromagnetic force for attracting particles having a first charge to a surface of the solid support and contacting the surface with the charged particles, which comprise the composition, and thereby coating the surface with the composition.

4. The method of claim 3, further comprising attaching the material to the solid support by applying one or more of the following processes:
   (i) storing the coated solid support for a period of time sufficient to increase the strength of bonding between solid support and the deposited polymers;
   (ii) generating reactive moieties in a deposited compound or in the solid support that react to form a covalent attachment between the polymer and the support;
   (iii) providing a reactive moiety incorporated into the support and reacting the polymer with the reactive moiety to covalently bond the compound to the surface;
   (iv) maintaining a field that attracts the charged particles to the support surface for a period of time sufficient to increase the strength of bonding between solid support and the polymer;
   (v) wetting the coated surface with a liquid sufficiently to solubilize a portion of the deposited polymers, but preferably without adding enough liquid to elute deposited compound from the solid support; and
   (vi) heating the coated surface.

5. The method of claim 3, comprising:

(1) in a first process, creating the electromagnetic force by directing ions of a second polarity opposite the first to the surface to create charges of the second polarity at the surface; or (2) in a second process, creating the electromagnetic force by creating an electrical field at a surface of the solid support.

6. The method of paragraph (1) of claim 5, further comprising controlling the amount of particle material adhering to the solid support by controlling the quantity of ions directed to the surface.

7. The method of paragraph (2) of claim 5, further comprising controlling the amount of particle material adhering to the solid support by using a sensing electrode to monitor particle depositions onto the sensing electrode under the influence of the field and removing the electric field or removing non-adherent charged particles when the sensing electrode indicates that a target level of particle depositions onto the sensing electrode.

8. An array of polymeric nucleic acid comprising spatially resolved nucleic acid probes deposited and attached on a solid support by electrostatic or controlled field deposition, wherein electrostatic deposition comprises forming an electrostatic charge on the surface effective to attract charged particles containing the polymeric nucleic acid to the surface, and controlled field deposition comprises forming an electromagnetic field effective to direct such charged particles to the surface.

9. A method of nucleic acid amplification comprising:
   (a) providing one or more primers of the amplification, wherein at least one primer is attached to a solid support,
   (b) contacting the solid support with a composition comprising sample material that prospectively contains a target nucleic acid from which an amplicon nucleic acid can be amplified as specified by the primers, and
   (c) if the sample contains the target nucleic acid, amplifying the amplicon by enzymatically replicating at least a first strand of the amplicon using at least bound primer.

10. A method of nucleic acid amplification comprising:

providing one or more primers for the amplification wherein at least one primer is attached to a solid support, contacting with the solid support a sample material that prospectively contains a target nucleic acid from which an amplicon nucleic acid can be amplified as specified by the primers, and amplifying the amplicon nucleic acid if the sample contains the target nucleic acid.

11. A device for conducting a chemical process on a solid support comprising:
   (1) a first layer of one or more releasable containers of liquid for supporting a chemical process that uses a sample that prospectively contains a target molecule that generates a responsive result in the chemical process;
   (2) a second layer of a first porous material on which are attached molecules of the samples, which molecules prospectively include target molecules; and
   (3) a bracket for bracing together the two layers;
wherein the liquid from the containers can be released from the containers to bath the first porous material.

12. The device of claim 11 for conducting nucleic acid amplifications wherein:

the liquid is for supporting a nucleic acid amplification reaction with a sample that prospectively contains a target nucleic acid from which a amplicon nucleic acid can be amplified as directed by amplification primers; and the nucleic acids of the samples are attached to the first porous material, wherein nucleic acids prospectively include target nucleic acids.

13. The apparatus of claim 11, wherein the first porous material contains a pattern of applications of material that prospectively contains target molecules.

14. The apparatus of claim 11, wherein the bracket further braces between the first and second layers a third layer of a second porous material.

15. The apparatus of claim 14, wherein on or in the second porous material there are deposited one or more reagents for supporting the chemical process.

16. A method of of detecting a target molecule using the device of claim 11 comprising the steps of:
   a) releasing the liquid from the releasable containers to bathe the first porous material; and
   b) when a target molecule is present, generating a responsive result.

17. The method of claim 9, wherein the amplifying further comprises enzymatically replicating a complimentary second strand of the amplicon.

18. The method of claim 9, further comprising:
   (d) providing on the solid support a spatially resolved array of distinct regions with primers attached to the solid support, the attached primers of two or more said regions selected for amplifying separate amplicons,
   (e) contacting all the two or more regions with each of one or more compositions that provide the enzymes and non-attached primers needed to support amplification, and
   (f) conducting an amplification such that two or more distinct amplicons are amplified and remain localized at their distinct respective regions.

19. The method of claim 18, further comprising:
   (g) amplifying in a plurality of the regions amplicons which provide a positive control verifying the operation of the amplification reaction, which control amplicons are synthesized using attached primers selected to generate such control amplicons.

* * * * *